United States Patent [19]

Ebi et al.

[11] Patent Number: 4,501,968
[45] Date of Patent: Feb. 26, 1985

[54] INFRARED RADIATION GAS ANALYZER

[75] Inventors: Hiroyuki Ebi; Kimio Miyatake, both of Kyoto, Japan

[73] Assignee: Horiba, Ltd., Kyoto, Japan

[21] Appl. No.: 471,455

[22] Filed: Mar. 2, 1983

[30] Foreign Application Priority Data

Mar. 9, 1982 [JP] Japan .............................. 57-33703[U]

[51] Int. Cl.³ ................................................ G01J 1/00
[52] U.S. Cl. ...................................... 250/343; 250/352
[58] Field of Search .................... 250/338 R, 343, 347, 250/352; 356/437

[56] References Cited

U.S. PATENT DOCUMENTS

| 3,794,838 | 2/1974 | Weiss et al. | 250/352 |
| 3,968,370 | 7/1976 | Luft | 250/343 |
| 4,233,513 | 11/1980 | Elder et al. | 250/352 |
| 4,373,137 | 2/1983 | Fabinski et al. | 250/343 |

FOREIGN PATENT DOCUMENTS 58-17343  2/1983  Japan ................... 356/437

*Primary Examiner*—Janice A. Howell
*Attorney, Agent, or Firm*—Wenderoth, Lind & Ponack

[57] ABSTRACT

An infrared radiation gas analyzer for determining the concentration of an ingredient in a sample gas has a sample gas container for containing a sample gas at a temperature at which the ingredient the concentration of which is to be determined will emit infrared radiation in a range characteristic of the ingredient and a window for allowing the infrared radiation to escape from the container. A pair of filters is provided, one of the filters transmitting only radiation in the range and the other of the filters transmitting only radiation in a range near to the firstmentioned range. A disc with the filters thereon rotates in front of the window for passing the filters across the path of radiation escaping from the container. An infrared radiation detector is positioned for receiving the radiation passed by the respective filters and emitting a pulsed signal, which is fed to a comparator for determining the difference between or the ratio of the respective pulses of the signal as an indication of the concentration of the ingredient the concentration of which is to be determined in the sample gas.

4 Claims, 5 Drawing Figures

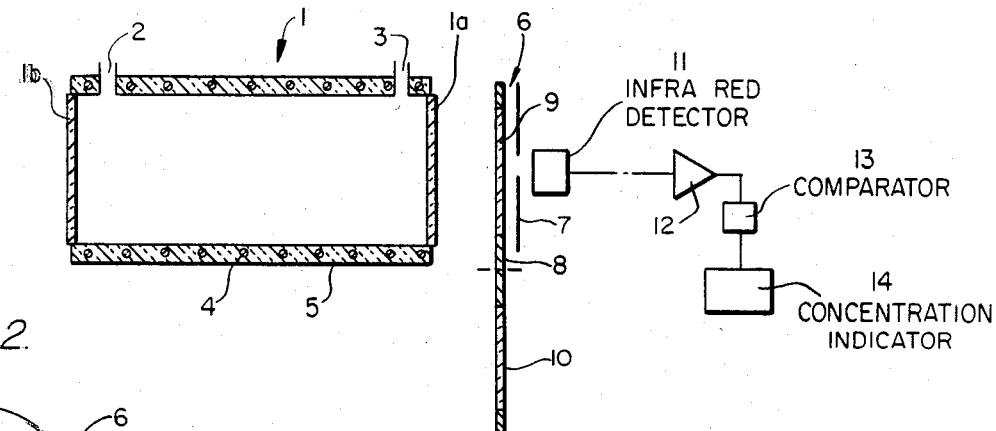
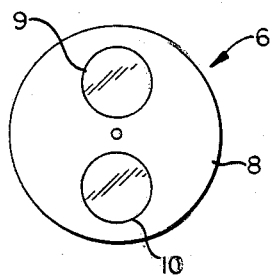
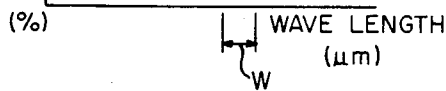
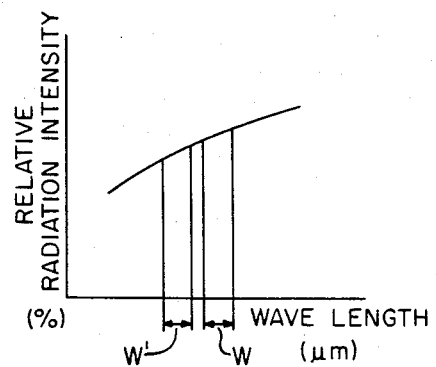
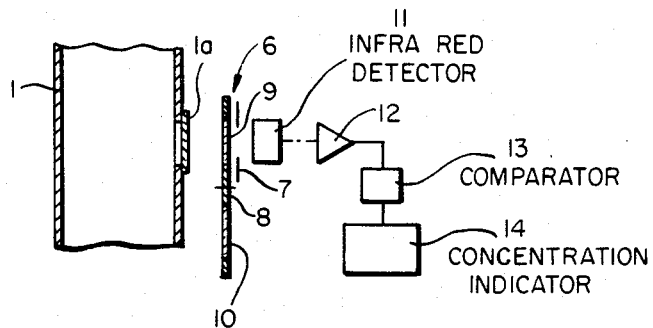

INFRARED RADIATION GAS ANALYZER

BACKGROUND OF THE INVENTION

1. Field of the Invention

The present invention relates to a gas analyzer for determining the concentration of specific ingredients in a sample gas.

2. Description of the Prior Art

The conventional method of determining concentration of ingredients in gas has been by a nondispersive infrared absorption analyzer using Lambert-Beer's law. However, such an analyzer requires an infrared light source and a power source for stabilizing said light source. In addition, it is expensive due to the complicated circuitry. Furthermore, the optical adjustment is required for adjusting the quantity of light incident upon a reference cell and the quantity of light incident upon a sample cell. The reference cell must be provided in order to prevent drift in the light source directing light on said sample cell from occurring.

OBJECTS AND BRIEF DESCRIPTION OF THE INVENTION

It is an object of the present invention to provide an operationally useful infrared radiation gas analyzer which can measure the concentration of ingredients in a gas with high accuracy, and which eliminates the main cause of errors in such measurement.

It is a further object to provide an infrared radiation gas analyzer for determining the concentration of specific ingredients in a sample gas which has simple construction and which is inexpensive.

To this end the present invention provides an infrared light source comprising means to measure an infrared radiation dose of a specified wave length constituted by radiation from gas molecules other than monoatomic molecules and produced by the gas when the gas molecules are heated to high temperatures, whereby an infrared light source and a power source for stabilizing said light source, which have heretofore been required in a conventional infrared gas analyzer, can be dispensed with.

BRIEF DESCRIPTION OF THE DRAWINGS

The invention will now be described in connection with the accompanying drawings, in which:

FIG. 1 is a schematic diagram of an infrared radiation gas analyzer according to the invention;

FIG. 2 is a front view of the chopper having filters thereon and used in the analyzer shown in FIG. 1;

FIGS. 3(a) and 3(b) are graphs showing relative radiation intensity; and

FIG. 4 is a schematic diagram of another embodiment of the present invention.

DESCRIPTION OF THE PREFERRED EMBODIMENT

Referring now to FIG. 1, a sample cell 1 has an inlet 2 for a sample gas under a particular pressure and an outlet 3 for the sample gas, the internal surface of said sample cell 1 being a mirror surface, and said sample cell 1 having cells windows $1a$ and $1b$ made of infrared ray-transmitting materials at the opposite ends thereof to transmit infrared radiation from within the sample cell. A heater 4 is provided in the wall of cell 1 for heating the sample gas in said sample cell 1, the heater having a capacity to heat the sample gas to temperatures of at least 100° C. to cause it to radiate infrared rays, in order to increase the radiation from a sample gas and decrease the background radiation relative to the radiation from the gas. Insulating material 5 surrounds the elements of heater 4.

A chopper 6 is provided in front of window $1a$ and has two filters therein spaced 180° from each other, as shown in FIG. 2, the chopper being positioned to rotate the filters successively past the window $1a$. The first filter 9 is for transmitting infrared rays having wave lengths in a specified range W and characteristic of those radiated from an ingredient the concentration of which in a sample gas is to be determined (for example a 4.3 $\mu$m band having a high relative radiation intensity when determining concentration of $CO_2$). The second filter 10 is for transmitting infrared rays having wave lengths in a range W' which is different from the above described specified range but near it. A plate 7 having a slit therein is positioned on the other side of the chopper 6 from the window $1a$.

An infrared detector 11 is positioned behind the slit in plate 7 for alternately receiving infrared rays transmitted through said first filter 9 and infrared rays transmitted through said second filter 10, and generating therefrom a pulsed electric signal the pulses of which have an amplitude corresponding to the intensity of the infrared radiation being transmitted through the filters. Solid detectors such as pyroelectric detectors can be satisfactorily used for said detector 11.

The output of detector 11 is amplified in an amplifier 12 and is supplied to a comparator 13 for obtaining the difference between or ratios of the amplitudes of the successive pulses of the electric signal from the detector. For example, when determining $CO_2$ concentration, said first filter 9 transmits infrared rays A+B or A×B, which is the total of infrared rays A radiated from only $CO_2$ and having wave lengths in the specified range W as shown in FIG. 3(a) and infrared rays B having wave lengths in said specified range W forming part of the background infrared rays as shown in FIG. 3(b), while said second filter 10 transmits the background infrared rays B' having wave lengths in the range W' near said specified range W. These background infrared rays are almost equal in intensity as shown in FIG. 3(b) so that B is nearly equal to B'. Accordingly, an indication of the approximate infrared radiation of the ingredient can be obtained by subtracting infrared radiation B' transmitted through said filter 10 from the infrared radiation A+B transmitted through said filter 9, i.e. A+B−B'≈A, or by dividing the radiation A×B transmitted through filter 9 by radiation B' transmitted through filter 10, i.e. (A×B)/B'≈A. Comparator 13 carries out the necessary operation and transmits the value of the radiation A to a concentration indicator 14 to indicate the concentration of the ingredient the concentration of which is to be determined.

In the above described apparatus, the total A+B or A×B of infrared rays A radiated from the ingredient the concentration of which is to be determined and background infrared rays B both having wave lengths in the specified range W, and background infrared rays B' having wave lengths in the range W' near to said specified range W are alternately received by said infrared detector 11 through said chopper 6 having the filters, and the concentration of the ingredient is indicated by said indicator 14 in accordance with the difference between the infrared radiation $A+B-B'$ or the ratio $(A \times B)/B'$. Thus accurate detection of the concentration is possible by substantially cancelling the background infrared radiation. The accurate detection of concentration from the difference in infrared radiation even though said cell 1 and said cell window 1a are contaminated or the temperatures thereof change so as to change the infrared radiation therefrom.

Alternatively, a construction in which said cell window 1b is omitted can be used. In the above described embodiment, a sample gas is introduced into the cell 1. However, an exhaust-gas pipe for exhausting exhaust gas from an internal combustion engine or a factory may be provided with a window which functions as said cell window 1a, and the chopper 6 provided with filters 8 and 9, the plate 7 and the infrared detector 11 positioned in front of such window 1a so that the concentration of an ingredient contained in a high temperature exhaust gas can be detected.

In the above embodiment, the chopper 6 is provided with the first filter 9 and the second filter 10. Alternatively the filters 9 and 10 may be separately formed. Various kinds of known detectors and filters can be used as the infrared detector 11 and filters 9 and 10. The concentrations of various components can be detected by employing as said filter 9 and 10 filters transmitting infrared rays in various ranges of wave lengths.

In the analyzer according to the present invention, neither an infrared light source nor a power source for stabilizing the light source, which are necessary in the conventional nondispersive infrared absorption analyzer, are required. Furthermore, neither a reference cell nor an optical adjusting mechanism for preventing drift of the light source are required. Thus the concentration of the specified ingredient contained in a sample gas can be determined by an analyzer having a simple and inexpensive construction.

The analyzer of the present invention takes into account the fact that infrared radiation incident upon an infrared detector may be changed by the radiation of infrared rays from the cell containing the ingredient and having the same wave length as the radiation from the ingredient the concentration of which is to be determined because of the high temperatures of the cells or the contamination of cells and cell-windows or a change in temperature thereof, and as a result the zero point is changed, which is an important factor causing errors of measurement in the detection of concentration. To overcome this drawback, the second filter was used to detect background infrared radiation by means of the infrared detector, and the infrared radiation from the ingredient the concentration of which is to be determined is determined from the difference or ratio between the infrared radiation radiated from the sample gas including background infrared rays, which are transmitted through the first filter, and radiation of background infrared rays, transmitted through the second filter. Thus, the concentration of the ingredient can be accurately determined by using an improved simplified gas analyzer in which infrared rays transmitted through the first filter, and infrared rays transmitted through the second filter are alternately directed onto a single infrared detector.

What is claimed is:

1. An infrared radiation gas analyzer for determining the concentration of an ingredient in a sample gas, comprising:
    a sample gas containing means for containing a sample gas at a temperature at which the ingredient the concentration of which is to be determined will emit infrared radiation in a range characteristic of the ingredient and means for allowing said infrared radiation to escape from said containing means;
    a pair of filters, one of said filters transmitting only radiation in said range and the other of said filters transmitting only radiation in a range near to said firstmentioned range;
    means for alternately passing said filters across the path of radiation escaping from said containing means;
    an infrared radiation detector positioned for receiving the radiation passed by said respective filters and emitting a pulsed signal;
    means for determining the difference between or the ratio of the respective pulses of said signal as an indication of the concentration of the ingredient the concentration of which is to be determined in the sample gas.

2. An infrared radiation gas analyzer as claimed in claim 1 in which said sample gas containing means is a sample gas container having heating means for heating a sample gas in said container.

3. An infrared radiation gas analyzer as claimed in claim 1 in which said sample gas containing means is a pipe for carrying a heated gas from a source of heated gas.

4. An infrared radiation gas analyzer as claimed in claim 1 in which said means for passing said filters comprises a rotatable disc having said filters thereon spaced circumferentially of said disc.

* * * * *